US012774949B2

(12) United States Patent
Tien

(10) Patent No.: US 12,774,949 B2
(45) Date of Patent: Oct. 27, 2026

(54) D-SHAPED OPTICAL FIBER GAS SENSOR

(71) Applicant: FENG CHIA UNIVERSITY, Taichung City (TW)

(72) Inventor: Chuen-Lin Tien, Taichung City (TW)

(73) Assignee: FENG CHIA UNIVERSITY, Taichung City (TW)

( * ) Notice: Subject to any disclaimer, the term of this patent is extended or adjusted under 35 U.S.C. 154(b) by 76 days.

(21) Appl. No.: 18/988,298

(22) Filed: Dec. 19, 2024

(65) Prior Publication Data

US 2026/0140046 A1 May 21, 2026

(30) Foreign Application Priority Data

Nov. 20, 2024 (TW) ................................ 113144634

(51) Int. Cl.
*G01N 21/31* (2006.01)
*G01N 33/00* (2006.01)

(52) U.S. Cl.
CPC ......... *G01N 21/31* (2013.01); *G01N 33/0027* (2013.01); *G01N 2201/08* (2013.01)

(58) Field of Classification Search
CPC . G01N 21/31; G01N 33/0027; G01N 2201/08
See application file for complete search history.

(56) References Cited

U.S. PATENT DOCUMENTS

2012/0029835 A1* 2/2012 Xia .................... G01N 21/0303 385/12
2019/0178860 A1* 6/2019 Hsueh .................. G01N 27/123
2022/0276179 A1 9/2022 Ohodnicki, Jr.
2023/0288359 A1* 9/2023 Mittermaier ......... G01N 27/124

FOREIGN PATENT DOCUMENTS

CN 103994985 B 3/2017
CN 109916861 A 6/2019

* cited by examiner

*Primary Examiner* — Georgia Y Epps
*Assistant Examiner* — Don J Williams
(74) *Attorney, Agent, or Firm* — RABIN & BERDO, P.C.

(57) ABSTRACT

A D-shaped optical fiber gas sensor comprises an optical fiber, a light source emitter connected with one terminal of the optical fiber, a spectrometer connected with the other terminal of the optical fiber, and a computer electrically connected with the spectrometer. The optical fiber is coated with a film with multiple gaps. When molecules of an under-test gas enter the multiple gaps of the film, a refractive index of the film will change. Lossy Mode Resonance arises in the film by a light emitted through the light source emitter, so that a light intensity of the light received by the spectrometer changes accordingly. The computer receives a light intensity detection value outputted by the spectrometer, and computes a gas detection concentration of the under-test gas that is corresponding to the light intensity detection value according to a linear model.

8 Claims, 6 Drawing Sheets

D-SHAPED OPTICAL FIBER GAS SENSOR

CROSS REFERENCE TO RELATED APPLICATIONS

The present application claims priority to Taiwan application No. 113144634, filed on Nov. 20, 2024, the content of which is hereby incorporated by reference in its entirety.

BACKGROUND OF THE INVENTION

1. Field of the Invention

The present invention relates to a gas sensor, especially a D-shaped optical fiber gas sensor based on an evanescent wave and Lossy Mode Resonance (LMR).

2. Description of the Related Art

Developments of science and technology have driven advancements of industrial zones and commercial areas surrounding the industrial zones. As a result, an amount of exhaust gas emitted by vehicles and factories has increased, the exhaust gas including, for example, carbon dioxide ($CO_2$), sulfur dioxide ($SO_2$), nitrogen dioxide ($NO_2$), and other types of gas that are harmful to the human or the environment. Therefore, government agencies or enterprises have gradually paid attention to monitor gas emissions in recent years.

For example, carbon dioxide sensors can be used to measure concentrations of carbon dioxide to monitor emissions of carbon dioxide. The carbon dioxide sensors can be classified according to different measurement principles and application environments. Common types of the carbon dioxide sensor include a chemical sensor, a capacitive sensor, etc. The chemical sensor adopts the principle of chemical reactions. When the carbon dioxide contacts a sensing material in the chemical sensor, the sensing material chemically reacts with the carbon dioxide, and properties (such as resistance) of the sensing material would be changed. The chemical sensor detects the change in the sensing material and converts the change into the concentration of carbon dioxide. The capacitive sensor adopts a characteristic that carbon dioxide can change a capacitance value of a capacitor to measure the concentration of carbon dioxide.

However, the environmental condition of the field whose carbon dioxide is to be monitored may be high temperature, high humidity, and/or high electromagnetic wave intensity. As a result, the above-mentioned carbon dioxide sensors have problems such as reduction of measurement accuracy, shortening of service life, etc., which are unfavorable for measuring the concentration of carbon dioxide.

SUMMARY OF THE INVENTION

Conventional gas sensors are not conducive to measurement of a gas concentration in monitoring areas under environmental conditions such as high temperature, high humidity, and high electromagnetic wave intensity. In view of this, the present invention provides a D-shaped optical fiber gas sensor, comprising:

an optical fiber having a first terminal and a second terminal opposite to each other, the optical fiber having a sensing section mounted in a measuring chamber filled with an under-test gas, a sensing cavity formed in the sensing section of the optical fiber, and a film mounted on a bottom surface of the sensing cavity, wherein the film is formed by a metal oxide and has multiple gaps;

a light source emitter connected with the first terminal of the optical fiber and emitting a light to the optical fiber;

a spectrometer connected with the second terminal of the optical fiber to receive the light from the optical fiber and to sense a light intensity of the light, and to output a light intensity detection value; and a computer electrically connected with the spectrometer to receive the light intensity detection value and to input the light intensity detection value into a linear model to compute a gas detection concentration of the under-test gas.

When the film of the D-shaped optical fiber gas sensor of the present invention is attached with molecules of the under-test gas, the molecules of the under-test gas can enter the multiple gaps of the film, so that the refractive index of the film will change. Lossy Mode Resonance arises in the film by the light incident from one terminal of the optical fiber, so that a light intensity of the light received by the spectrometer connected to the other terminal of the optical fiber changes accordingly. The computer receives the light intensity detection value outputted by the spectrometer, and computes the gas detection concentration of the under-test gas that is corresponding to the light intensity detection value according to the linear model. Compared with common gas sensors described in the prior art, the optical fiber of the present invention can still operate normally even if the optical fiber is placed in an environment under conditions such as high temperature, high humidity, etc., so that a service life of the D-shaped optical fiber gas sensor of the present invention can be extended. Moreover, the optical fiber has a characteristic of not being interfered by electromagnetic waves and can maintain high measurement accuracy, thereby expanding applicable fields of the present invention, such as industrial environment monitoring, smart home, etc.

DETAILED DESCRIPTION OF THE INVENTION

In order to understand the technical characteristics and practical effects of the prevent invention in detail, and accomplish them according to the content of the present invention, the detailed description is as follows with the embodiments shown in the figures.

Figure 1:
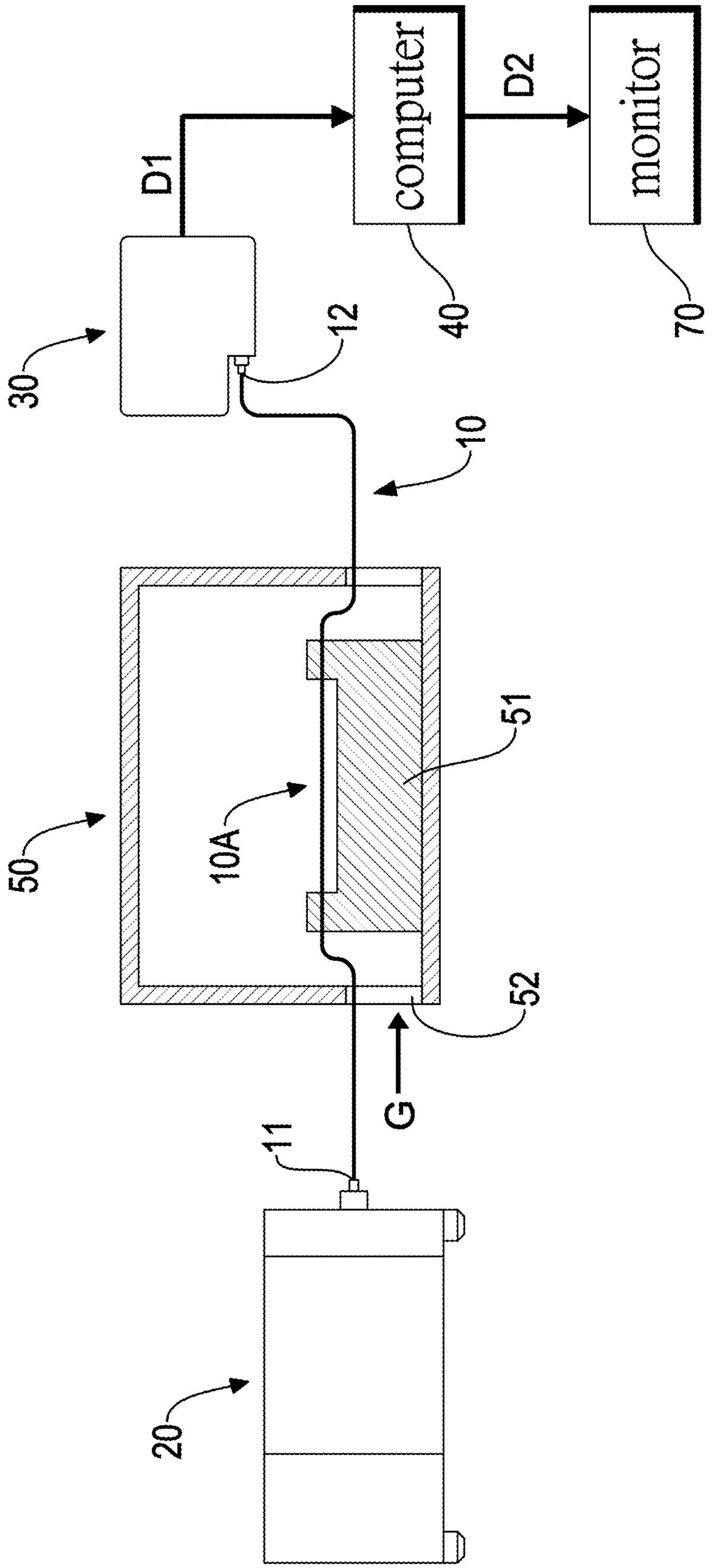
FIG. 1 is a circuit block diagram of a D-shaped optical fiber gas sensor of the present invention.
Figure 2:
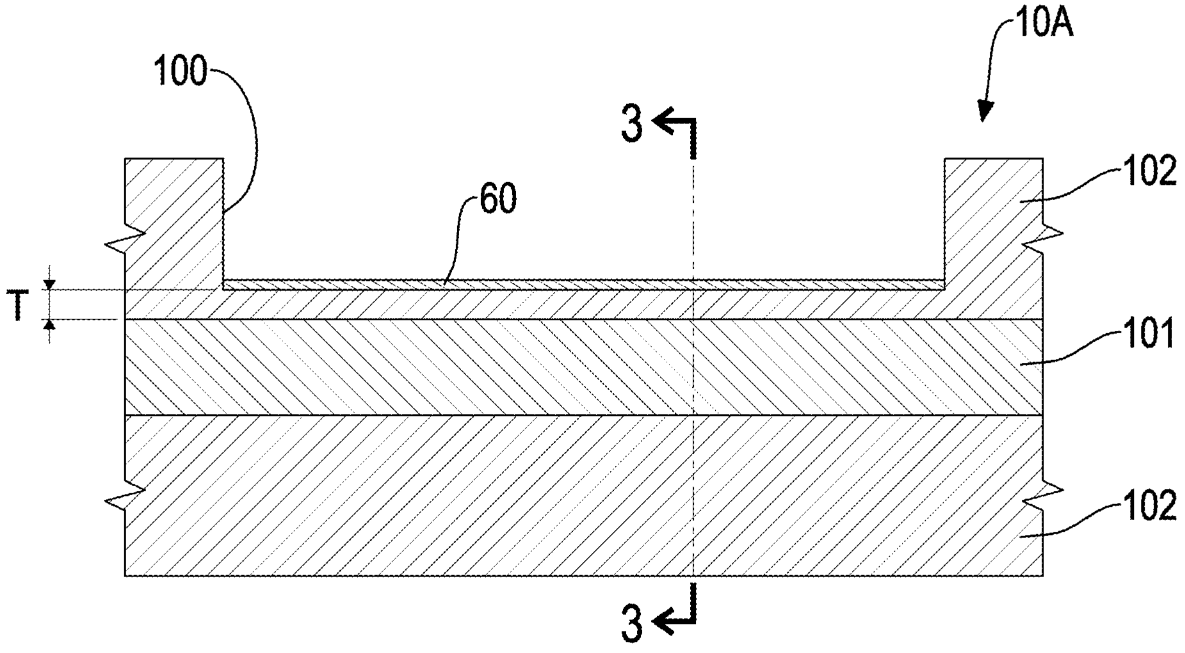
FIG. 2 is a cross-sectional side view of an optical fiber of the D-shaped optical fiber gas sensor of the present invention.

Referring to FIG. 1 and FIG. 2, a D-shaped optical fiber gas sensor of the present invention comprises an optical fiber 10, a light source emitter 20, a spectrometer 30, and a computer 40 to form a sensing system, a sensing device, etc. The optical fiber 10 passes through a measuring chamber 50 filled with an under-test gas G. In particular, a base 51 is mounted in the measuring chamber 50. The base 51 is adapted to fix a section (hereinafter defined as a sensing section 10A) of the optical fiber 10, so that the sensing section 10A of the optical fiber 10 can be in a straightened state in the measuring chamber 50. The measuring chamber 50 has an air inlet 52. The air inlet 52 is adapted to allow the under-test gas G to enter the measuring chamber 50. For example, the under-test gas G can be gas of carbon dioxide ($CO_2$).

Figure 3:
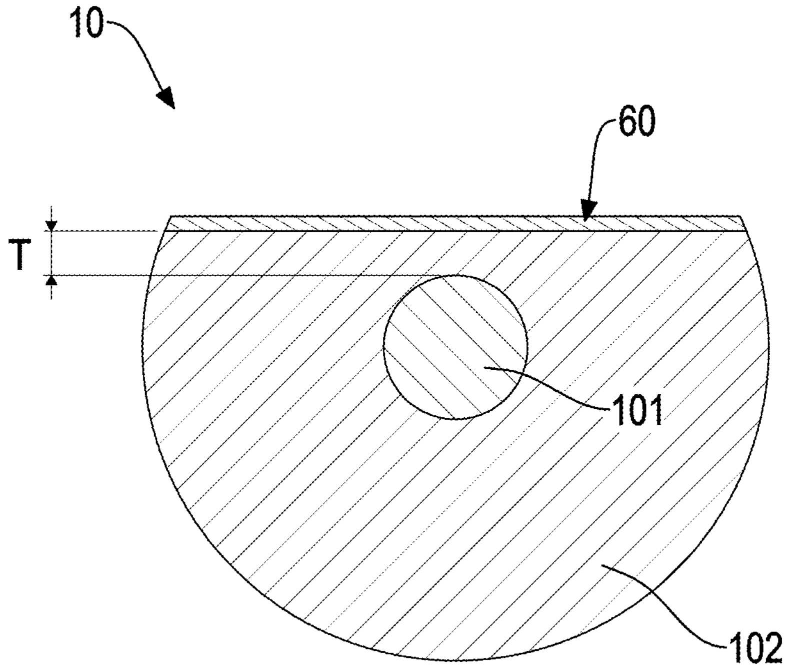
FIG. 3 is a cross-sectional side view of the optical fiber of the D-shaped optical fiber gas sensor of the present invention.

The optical fiber 10 has a first terminal 11 and a second terminal 12 opposite to each other. The first terminal 11 is connected with the light source emitter 20, and the second terminal 12 is connected with the spectrometer 30. A sensing cavity 100 is formed in the sensing section 10A of the optical fiber 10, and the optical fiber is mounted with a film 60 on a bottom surface of the sensing cavity 100. Specifically, referring to FIG. 2 and FIG. 3, the optical fiber 10 has a core layer 101 and a cladding layer 102. The cladding layer 102 surrounds the core layer 101, and a refractive index of the core layer 101 is greater that a refractive index of the cladding layer 102. The sensing cavity 100 is formed in the cladding layer 102. That is, a part of the cladding layer 102 is between the film 60 and the core layer 101, and the foregoing part of the cladding layer 102 between the film 60 and the core layer 101 has a thickness T. For example, the thickness can be 3 micrometers.

For example, the optical fiber 10 can be a Single Mode Fiber (SMF), a Multiple Mode Fiber (MMF), etc. The present invention is not limited to the foregoing examples. In brief, an example of mounting the film 60 on the optical fiber 10 comprises steps as follows:

1. Polishing the cladding layer 102 of the optical fiber 10 to form the sensing cavity 100, wherein the optical fiber 10 needs to be in the straightened state during the polishing process to reduce possibility of breakage of the optical fiber 10.
2. Cleaning the sensing cavity 10, then connecting the light source emitter 20 with the first terminal 11 of the optical fiber 10, and connecting the spectrometer 30 with the second terminal 12 of the optical fiber 10, wherein the light source emitter 20 and the spectrometer 30 can be adapted to confirm whether there are any defects in the optical fiber 10 before coating.
3. Coating the film 60 on the bottom surface of the sensing cavity 100. For example, the film 60 can be coated on the bottom surface of the sensing cavity 100 through an E-beam evaporator, and a thickness of the film 60 can be 80 to 90 nanometers.

Figure 4:
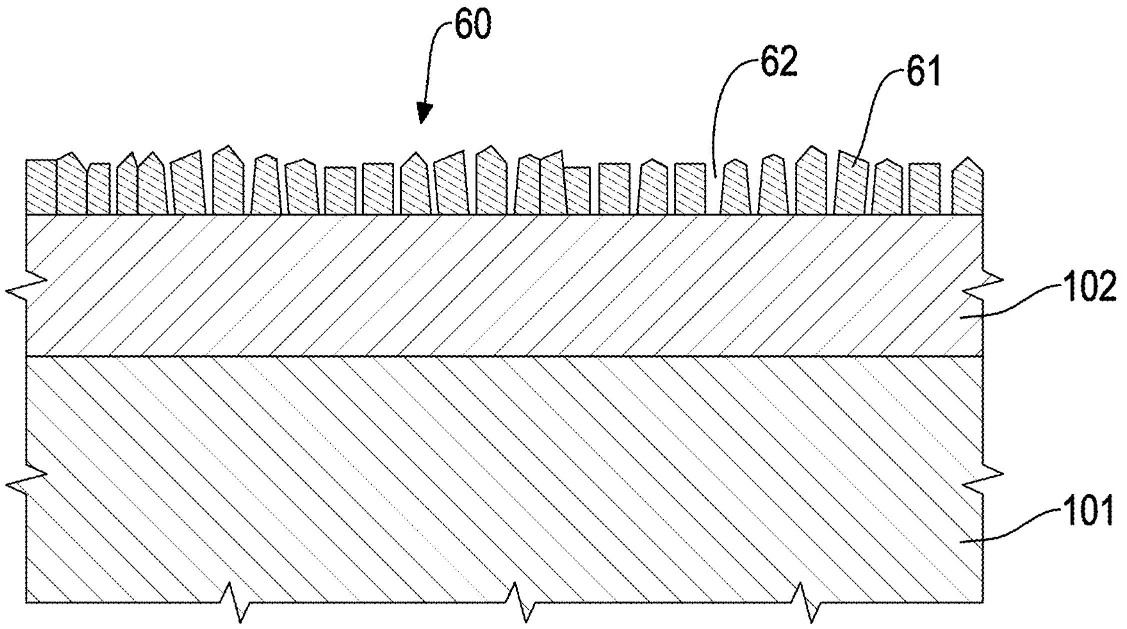
FIG. 4 is an enlarged cross-sectional side view of a partial section of the optical fiber of the D-shaped optical fiber gas sensor of the present invention.

Referring to FIG. 4, the microstructure of the film 60 includes multiple pillars 61. A bottom of each pillar 61 is connected with the bottom surface of the sensing cavity 100 of the optical fiber 10, wherein the multiple pillars refer to tiny structures (such as nanostructures) of the films observed under a Scanning Electron Microscope (SEM) or a Transmission Electron Microscope (TEM), and multiple gaps 62 are formed among the multiple pillars 61. For example, some of the multiple pillars 61 are separated from one another. That is, a gap 62 is between two adjacent pillars 61. Alternatively, several pillars 61 cluster together as a pillar group, and a gap 62 is between two adjacent pillar groups. Alternatively, a gap 62 is between adjacent pillar group and pillar 61. Preferably, the gap 62 extends from a top surface of the pillar 61 to the bottom surface of the sensing cavity 100. Moreover, a density of the multiple gaps 62 is adapted to control a transient response variation and a sensitivity of the D-shaped optical fiber gas sensor. For example, the film 60 can be formed by a metal oxide, such as zinc oxide (ZnO), tungsten trioxide ($WO_3$), tin dioxide ($SnO_2$), etc. The present invention is not limited to the foregoing examples.

Referring to FIG. 1, the light source emitter 20 emits a light, and the light is incident from the first terminal 11 of the optical fiber 10 toward the second terminal 12 of the optical fiber 10 and so outputted from the second terminal 12 of the optical fiber 10. The spectrometer 30 connected with the second terminal 12 would receive the light. Specifically, the light is incident from the core layer 101 of the optical fiber 10. Since the refractive index of the core layer 101 is greater than the refractive index of the cladding layer 102, and an incident angle of the light is greater than a critical angle, the light can be transmitted from the first terminal 11 to the second terminal 12 through total internal reflection in the core layer 101 of the optical fiber 10.

Moreover, since the light is incident from an optically dense medium (the core layer 101) to an optically sparse medium (the cladding layer 102), an evanescent wave will be formed in the optically sparse medium (the cladding layer 102). The evanescent wave propagates along a contact surface between the core layer 101 and the cladding layer 102. When the light travels through the core layer 101 corresponding to the film 60 as shown in FIG. 2, and a value of the thickness T of the cladding layer 102 is less than a threshold, the evanescent wave formed in the cladding layer will couple to the film 60. That is, the evanescent wave is also formed in the film 60, and Lossy Mode Resonance (LMR) arises in the film 60 by the evanescent wave.

Referring to FIG. 1, the spectrometer 30 senses a light intensity of the light emitted from the second terminal 12 to output a light intensity detection value D1. The computer 40 is electrically connected with the spectrometer 30 to receive the light intensity detection value D1. The computer 40 inputs the light intensity detection value D1 into a linear model to compute a gas detection concentration D2 of the under-test gas G in the measuring chamber 50. In particular, the spectrometer 30 senses the light intensity of the light emitted from the second terminal 12 to generate a spectral energy distribution curve. The spectral energy distribution curve includes corresponding relationships between multiple light intensity detection values D1 and multiple wavelengths. That is, the light has different light intensity detection values at different wavelengths. The computer 40 receives the spectral energy distribution curve and captures the light intensity detection value D1 of a specific wavelength in the spectral energy distribution curve, and inputs the light intensity detection value D1 to the linear model to compute the gas detection concentration D2.

The linear model can be established by data obtained from a gas sensing concentration experiment. The gas sensing concentration experiment is described as follows.

Figure 5:
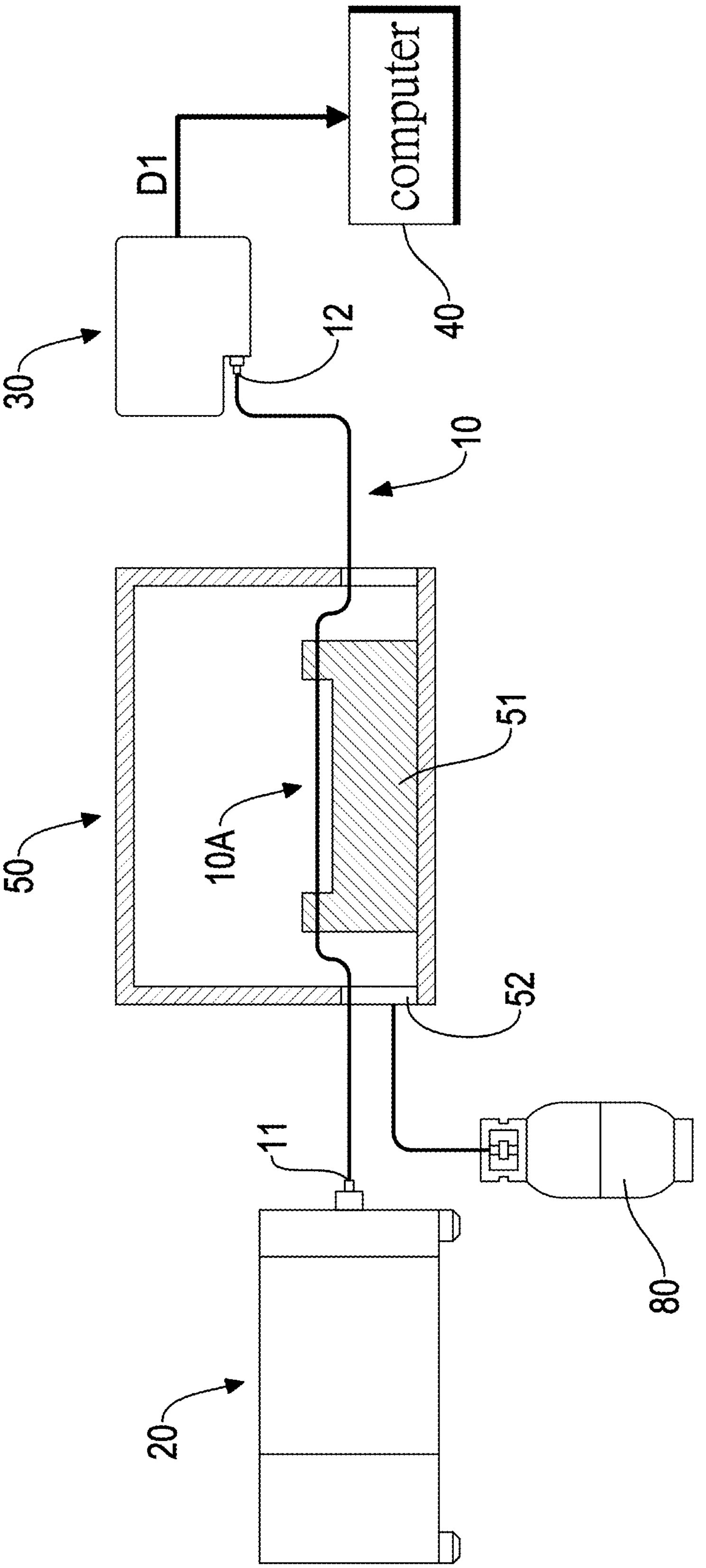
FIG. 5 is a circuit block diagram of a gas sensing concentration experiment of the D-shaped optical fiber gas sensor of the present invention.
Figure 6:
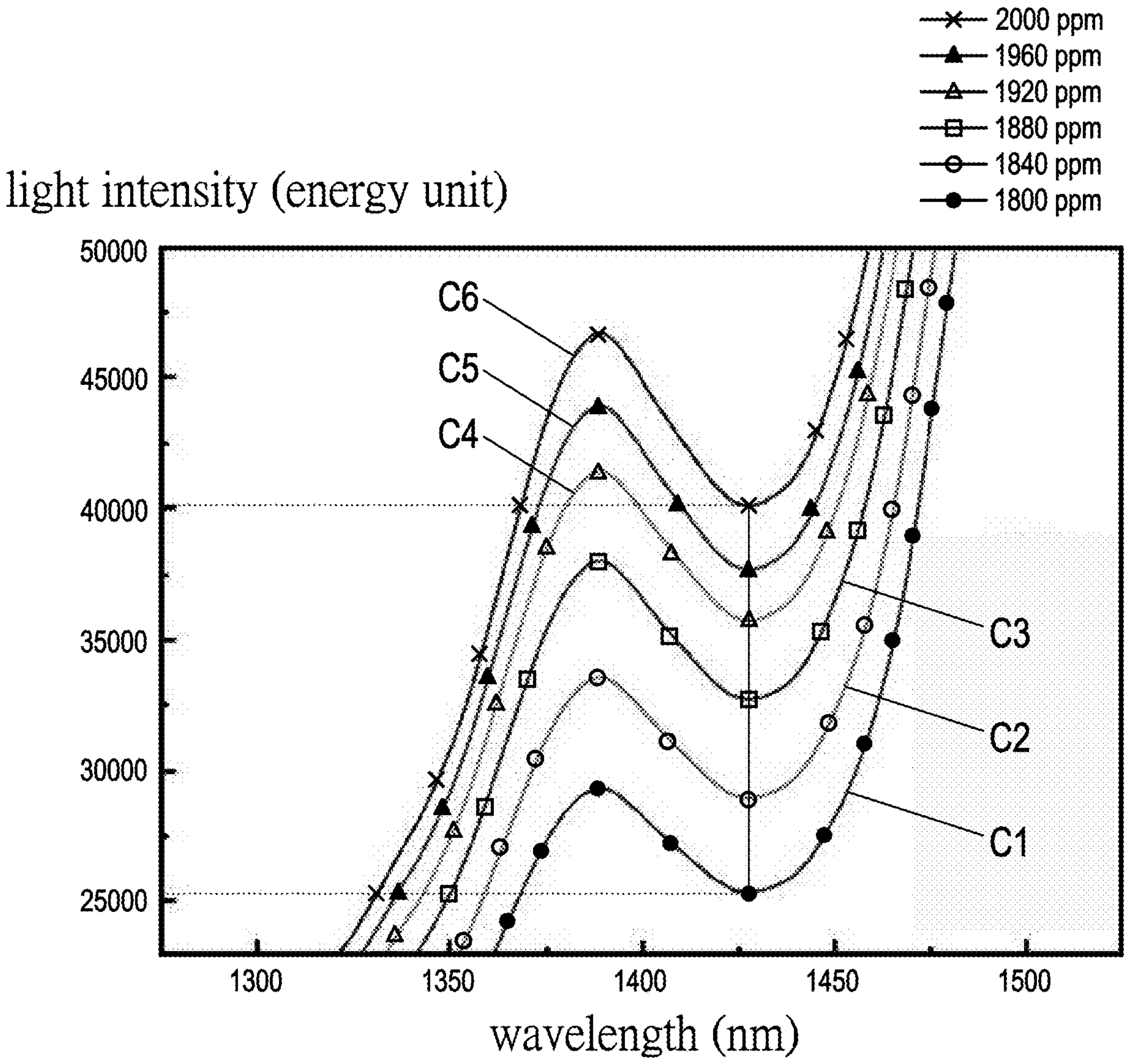
FIG. 6 is a schematic diagram of spectral energy distribution curves corresponding to different gas reference concentrations.

Referring to FIG. 5, the measuring chamber 50 can be connected with a gas cylinder 80 through a pipe to fill the measuring chamber 50 with an experimental gas and control a concentration of the experimental gas. For example, the experimental gas can be gas of carbon dioxide ($CO_2$). At first, the experiment is to control the concentration of the experimental gas to be a first gas reference concentration (such as 1800 ppm), and to operate the light source emitter 20 to emit the light. The spectrometer 30 receives the light to generate a first spectral energy distribution curve C1 as shown in FIG. 6, and the computer 40 receives and stores information of the first spectral energy distribution curve C1. A next step is to control the concentration of the experimental gas to be a second gas reference concentration (such as 1840 ppm), and to operate the light source emitter 20 to emit the light. The spectrometer 30 receives the light to generate a second spectral energy distribution curve C2 as shown in FIG. 6, the computer 40 receives and stores information of the second spectral energy distribution curve C2. The experiment will repeat the abovementioned steps until a sufficient number of multiple spectral energy distribution curves are stored in the computer 40, such as the first spectral energy distribution curve C1 to a sixth spectral energy distribution curve C6 as shown in FIG. 6. Moreover, the multiple spectral energy distribution curves respectively correspond to different gas reference concentrations.

The computer 40 captures and stores a value of each spectral energy distribution curve as a light intensity reference value corresponding to each spectral energy distribution curve. That is, the computer 40 stores multiple intensity reference values. For example, each spectral energy distribution curve has a peak and a trough. The computer 40 captures a value of the trough as the light intensity reference value of each spectral energy distribution curve. Since the multiple spectral energy distribution curves respectively correspond to the different gas reference concentrations, the multiple light intensity reference values respectively correspond to the multiple gas reference concentrations. That is, the multiple light intensity reference values are different to one another, and the multiple gas reference concentrations are different to one another.

When gas molecules are attached to the film 60, a material carrier concentration of the film 60 will change accordingly, causing the refractive index of the film 60 to change. Specifically, the gas molecules of the under-test gas G enter the multiple gas 62 of the film 60 and adhere to side walls of the pillar 61, thereby changing the refractive index of the film 60. As the gas reference concentration gradually increases, the refractive index of the film 60 will gradually increase. The Lossy Mode Resonance generated by the light in the film 60 will be enhanced, thereby increasing the light intensity of the light emitted from the second terminal 12 of the optical fiber 10. That is, a higher gas reference concentration corresponds to a higher light intensity reference value.

Then, the computer 40 performs linear fitting according to the multiple light intensity reference values and the multiple gas reference concentrations to generate the linear model. The computer 40 stores the linear model as a basis for determination of the D-shaped optical fiber gas sensor. That is, when the computer receives the light intensity detection value D1, the computer 40 executes the linear model to compute the gas detection concentration D2 corresponding to the light intensity detection value D1. In addition, referring to FIG. 1, in an embodiment of the present invention, the computer 40 is connected with a monitor 70. The monitor 70 receives and displays information of the gas detection concentration D2 of the under-test gas G.

The D-shaped optical fiber gas sensor of the present invention adopts the optical fiber 10 (D-shaped optical fiber) coated with the film 60 as a gas sensing component. When the film 60 is attached with molecules of the under-test gas G, the refractive index of the film 60 will change. Lossy Mode Resonance arises in the film 60 by the light incident from one terminal of the optical fiber 10, so that the light intensity of the light received by the spectrometer 30 connected to the other terminal of the optical fiber 10 changes accordingly. The spectrometer 30 is connected with the computer 40, and the computer 40 receives the light intensity detection value D1 outputted by the spectrometer 30. The computer 40 computes a gas detection concentration D2 of the under-test gas G that is corresponding to the light intensity detection value D1 according to the linear model. Compared with common gas sensors described in the prior art, the optical fiber 10 of the present invention can still operate normally even if the optical fiber 10 is placed in an environment under conditions such as high temperature, high humidity, etc., so that a service life of the D-shaped optical fiber gas sensor can be extended. Moreover, the optical fiber 10 has a characteristic of not being interfered by electromagnetic waves and can maintain high measurement accuracy, therefore expanding applicable fields of the present invention, such as industrial environment monitoring, smart home, etc.

The above only records the implementations or embodiments of the technical artifices adopted by the present invention to solve the problems, and is not configured to limit the claims of the present invention. That is, all equivalent changes and modifications that are consistent with the meaning of the claims of the present invention or made in accordance with the claims of the present invention are covered by the claims of the present invention.

What is claimed is:

1. A D-shaped optical fiber gas sensor, comprising:

an optical fiber having a first terminal and a second terminal opposite to each other, the optical fiber having a sensing section mounted in a measuring chamber filled with an under-test gas, a sensing cavity formed in the sensing section of the optical fiber, and a film mounted on a bottom surface of the sensing cavity, wherein the film is formed by a metal oxide and has multiple gaps for gas molecules to attach, causing a refractive index of the film to change;

a light source emitter connected with the first terminal of the optical fiber and emitting a light to the optical fiber;

a spectrometer connected with the second terminal of the optical fiber to receive the light from the optical fiber and to sense a light intensity of the light, and to output a light intensity detection value; and a computer electrically connected with the spectrometer to receive the light intensity detection value and to input the light intensity detection value into a linear model to compute a gas detection concentration of the under-test gas, wherein the optical fiber has a core layer and a cladding layer, the cladding layer surrounding the core layer, the sensing cavity being formed in the cladding layer; and an evanescent wave is formed by the light traveling through the film and the cladding layer between the film and the core layer.

2. The D-shaped optical fiber gas sensor as claimed in claim 1, wherein:

the film comprises multiple pillars, a bottom of each pillar is connected with the bottom surface of the sensing cavity, and the multiple gaps are formed among the multiple pillars.

3. The D-shaped optical fiber gas sensor as claimed in claim 1, wherein the metal oxide is zinc oxide.

4. The D-shaped optical fiber gas sensor as claimed in claim 1, wherein the metal oxide is tungsten trioxide.

5. The D-shaped optical fiber gas sensor as claimed in claim 1, wherein the metal oxide is tin dioxide.

6. The D-shaped optical fiber gas sensor as claimed in claim 1, wherein:

the computer stores multiple light intensity reference values and multiple gas reference concentrations, the multiple light intensity reference values respectively correspond to the multiple gas reference concentrations, the multiple light intensity reference values are different to one another, and the multiple gas reference concentrations are different to one another;

the computer performs linear fitting according to the multiple light intensity reference values and the multiple gas reference concentrations to generate the linear model.

7. The D-shaped optical fiber gas sensor as claimed in claim 6, wherein:

the computer stores information of multiple spectral energy distribution curves generated by the spectrometer, the multiple spectral energy distribution curves respectively correspond to the gas reference concentrations, each spectral energy distribution curve has a peak and a trough, and a value of the trough is the light intensity reference value.

8. The D-shaped optical fiber gas sensor as claimed in claim 1, wherein:

the computer is connected with a monitor, and the monitor receives and displays information of the gas detection concentration of the under-test gas.

* * * * *